(12) United States Patent
Mukerjee et al.

(10) Patent No.: US 6,342,621 B1
(45) Date of Patent: Jan. 29, 2002

(54) RUTHENIUM CATALYSTS FOR METATHESIS REACTIONS OF OLEFINS

(75) Inventors: Shakti L. Mukerjee, Louisville, KY (US); Vernon L. Kyllingstad, Floyds Knobs, IN (US)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/492,746

(22) Filed: Jan. 27, 2000

Related U.S. Application Data

(60) Provisional application No. 60/118,074, filed on Jan. 29, 1999.

(51) Int. Cl.$^7$ .............................. C07F 15/00; C07F 9/02; B01J 31/00
(52) U.S. Cl. ............................. 556/21; 556/18; 556/22; 556/136; 556/137; 549/206; 546/2; 526/160; 526/161; 526/169.1; 526/281; 526/282; 526/283; 502/155; 502/162
(58) Field of Search .................... 556/18, 21, 22, 556/136, 137; 502/155, 162; 526/281, 282, 283, 160, 161, 169.1; 546/2; 549/206

(56) References Cited

U.S. PATENT DOCUMENTS

| | | | |
|---|---|---|---|
| 4,883,851 A | 11/1989 | Grubbs et al. | 526/268 |
| 5,198,511 A | 3/1993 | Brown-Wensley et al. | 526/113 |
| 5,312,940 A | 5/1994 | Grubbs et al. | 556/136 |
| 5,468,819 A | 11/1995 | Goodall et al. | 526/171 |
| 5,554,778 A | 9/1996 | Beatty et al. | 556/21 |
| 5,559,262 A | 9/1996 | Beatty et al. | 556/20 |
| 5,569,730 A | 10/1996 | Goodall et al. | 526/282 |
| 5,599,962 A | 2/1997 | Beatty et al. | 556/21 |
| 5,677,405 A | 10/1997 | Goodall et al. | 526/281 |
| 5,689,003 A | 11/1997 | Beatty et al. | 564/278 |
| 5,710,298 A | 1/1998 | Grubbs | 556/22 |
| 5,728,785 A | 3/1998 | Grubbs et al. | 526/142 |
| 5,728,917 A | 3/1998 | Grubbs et al. | 585/683 |
| 5,750,815 A | 5/1998 | Grubbs et al. | 585/511 |
| 5,811,515 A | 9/1998 | Grubbs et al. | 530/530 |
| 5,831,108 A | 11/1998 | Grubbs et al. | 556/21 |

FOREIGN PATENT DOCUMENTS

WO    WO 98/21214    5/1998

OTHER PUBLICATIONS

Cox, et al., J. Chem. Soc. Dalton Trans., 1991, pp 2013–2018.
Fu, et al., J. Am. Chem. Soc., 1993, 115, pp 9856–9857.
Herrmann, et al., Angew. chem. Int. Ed Engl., 1996, 35 No. 10, pp 1087–1088.
Schrock, et al., J. Am. chem. Soc., 1990, 112, pp 3875–3886.
Nguyen, et al., J. Am. Chem. Soc., 1992, 114 pp 3974–3975.
Cox, et al., Inorg. Chem., 1990, 29, pp 1360–1365.
Cox, et al., J. Chem. Soc., Chem. Commun., 1988, pp 951–953.
Porri, et al., Tetrahedron Letters No. 47, 1965, pp. 4187–4189.
Abstract of EP 839,821–A2 (May 6, 1998).

*Primary Examiner*—Porfirio Nazario-Gonzalez
(74) *Attorney, Agent, or Firm*—Armstrong, Westerman, Hattori, McLeland & Naughton, LLP

(57) ABSTRACT

Penta-coordinated ruthenium catalysts for the metathesis reactions of olefins, in particular ring opening metathesis polymerization (ROMP) of cyclo-olefin monomers, which are cationic complexes represented by formula I, II or III:

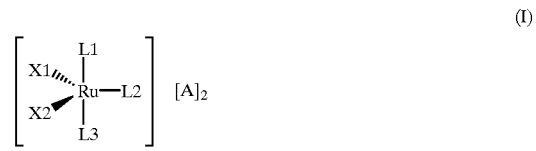

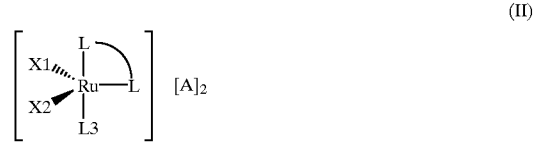

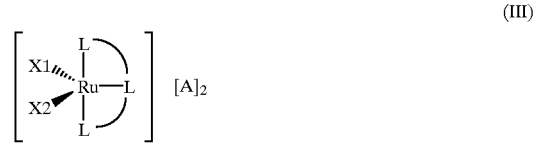

wherein each of $X^1$ and $X^2$, which may be the same or different, is an optionally substituted $C_3$–$C_{20}$ hydrocarbon group having an allyl moiety as an end group bonded to the ruthenium atom, or $X^1$ and $X^2$ together form a group, optionally substituted, which results from dimerization of an alkene and has at each end an allyl group bonded to the ruthenium atom; $L^1$ and $L^2$ are mono-dentate neutral electron donor ligands, preferably highly sterically encumbered neutral electron donor ligands such as alkyl phosphines or amines; L^L is a bidentate neutral electron donor ligand, preferably phosphine, amino, imino, arsine or arphos; $L^3$ is a solvent molecule or a neutral mono-dentate electron donor ligand; L^L^L is a tridentate electron donor ligand, preferably phosphorus or nitrogen containing ligand; and [A] is a counter anion weakly coordinated to the ruthenium atom.

54 Claims, No Drawings

RUTHENIUM CATALYSTS FOR METATHESIS REACTIONS OF OLEFINS

This application claims the benefit of the filing date of provisional application No. 60/118,074 filed Jan. 29, 1999.

The present invention relates to highly active catalysts for olefin metathesis reactions, and the preparation of the catalysts. The invention also relates to the olefin metathesis reactions catalyzed with the catalysts of the invention.

BACKGROUND

The past several years have witnessed a healthy surge in catalyst development related to metathesis reactions of olefins, in particular metathesis polymerization of olefins. These well defined catalysts usually possess a metal-carbon double bond (metal-carbene or alkylidene) that can coordinate to the alkene moiety of the olefin, and in particular, can perform the ring opening of cyclo-olefin monomers in a rather facile manner. Most of the metals that exhibit remarkable activity for this phenomenon are second-or third-row mid-to late- transition metals. Although the specific reason for this observation has not been clearly articulated, many theories have been proposed, the most prevalent of which is that late transition metals exhibit greater robustness towards the impurities that may inherently be present within a reaction system and, consequently, catalysts containing those metals resist degradation.

Among olefins, cyclo-olefin monomers like norbornene (NB) or dicyclopendadiene (DCPD) which possess a strained double bond can readily undergo ring opening metathesis polymerization (ROMP) because the ring opened product is thermodynamically favored. For ring opening to occur in these cyclo-olefins there is no pre-requisite for the catalyst to possess a metal-carbene moiety in its framework, because any organometallic complex that has the capability of initiating a metal-carbene formation in situ can also perform as a catalyst. For instance, it is well known that $RuCl_3 \cdot 3H_2O$ can accomplish the ROMP of NB quite effortlessly, even though there is no carbene present in the catalyst. It is hypothesized that the first step of the reaction, when the metal halide reacts with the monomer, is the formation of a metal carbene moiety that is responsible for further polymer propagation.

The catalysts that have received the greatest exposure in the literature by far are those designed by Schrock et al., as reported in Schrock et al., *J. Am. Chem. Soc.*, 1990, 112, 3875, and by Grubbs's group, as reported in Fu et al., *J. Am. Chem. Soc.*, 1993, 115, 9856; Nguyen et al., *J. Am. Chem. Soc.*, 1992, 114, 3974; and Grubbs et al., WO98/21214 (1998). The Grubbs catalyst (a ruthenium carbene) is slightly more versatile than the Schrock catalyst (a molybdenum alkylidene) because of its ease of synthesis as well as its utility from a commercial viewpoint. Cox and co-workers reported in Cox et al., *Inorg. Chem.*, 1990, 29, 1360; Cox, et al., *J. Chem. Soc., Chem. Commun.*, 1988, 951–953; and Porri et al, *Tetrahedron Letters*, No. 47., 1965, 4187–4189, the synthesis of a class of metal catalysts based on ruthenium metal. These catalysts consist primarily of a bis-allyl ligand wrapping the metal, along with two or three acetonitrile ligands. Additionally, these catalysts possess a mono- or di-anion that is virtually (i.e., almost) coordinated to the metal center, which is therefore considered to be formally in the +4 oxidation state. These complexes in conjunction with diazo ethyl acetate have been used by Herrmann's group, as reported in Herrmann et al., *Angew. Chem. Int'l. Ed. Engl.*, 1996, 35, 1087, to investigate the polymerization (specifically the ROMP) of NB. Herrmann has conjectured that the active species in the catalyst system is a metal carbene generated in situ when the ruthenium reacts with the diazo alkyl compound (such as diazo ethyl acetate).

A disadvantage of the above catalysts is that for the ROMP of cyclic olefins these catalysts must be used with a co-catalyst such as a diazo alkyl compound, which requires special caution in handling because of the instability of the diazo group.

SUMMARY OF THE INVENTION

One aspect of the invention is to provide catalysts which are highly active in initiating metathesis reactions in olefins.

Another aspect of the invention is to provide catalysts which are highly active in the ring-opening polymerization (ROMP) of cyclo-olefin monomers without requiring the presence of a co-catalyst such as a diazo alkyl compound.

Another aspect of the invention is to provide methods for the preparation in good yield of the catalysts for metathesis reactions in olefins.

Yet another aspect of the invention is to provide a highly effective method for polymerizing olefins, in particular cyclo-olefins, using the catalysts of the invention.

DESCRIPTION OF THE INVENTION

The catalysts of the invention are characterized by a complex cation represented by the formula I*, II* or III* below, wherein the ruthenium atom is in the 4+ oxidation state, has an electron count of 14, and is penta-coordinated.

(I*)

(II*)

(III*)

wherein
each of $X^1$ and $X^2$, which may be the same or different, is a $C_3$–$C_{20}$ hydrocarbon group having an allyl moiety as an end group bonded to the ruthenium atom, optionally substituted with a $C_1$–$C_{20}$ alkyl, a $C_1$–$C_{20}$ alkoxy, or a $C_6$–$C_{12}$ aryl group on its backbone, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; or $X^1$ and $X^2$ together form a group which results from dimerization of an alkene and has at each end an allyl group bonded to the ruthenium atom, said group resulting from the alkene dimerization being optionally substituted on its backbone with a $C_1$–$C_{20}$ alkyl, a $C_1$–$C_{20}$ alkoxy, or a $C_6$–$C_{12}$ aryl group, and further optionally having a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen;

$L^1$ and $L^2$, which may be the same or different, are monodentate neutral electron donor ligands;

$L^3$ is a solvent molecule coordinated to the central ruthenium atom or a neutral monodentate electron donor ligand;

$L^\frown L$ is a bidentate neutral electron donor ligand; and $L^\frown L^\frown L$ is a neutral tridentate electron donor ligand.

More specifically, the catalysts of the invention are cationic complexes represented by the formula I, II or III below, wherein the ruthenium complex cation is paired with a counter anion A.

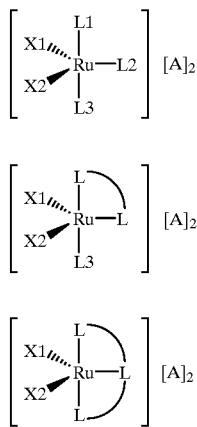

wherein $X^1$, $X^2$, $L^1$, $L^2$, $L^3$, $L^\frown L$ and $L^\frown L^\frown L$ are as described above, and A is a counter anion which is weakly coordinated to the central ruthenium atom in the complex cation.

The neutral electron donor ligand as recited in the definition of $L^1$, $L^2$, $L^3$, $L^\frown L$ and $L^\frown L^\frown L$ in the complex cations of the invention is any ligand which, when removed from the central ruthenium atom in its closed shell configuration, has a neutral charge, i.e., is a Lewis base. Preferably, at least one of the monodentate neutral electron donor ligands in the complex cation is a sterically encumbered ligand. Examples of sterically encumbered monodentate ligands are phosphines, sulfonated phosphines, phosphites, phosphinites, phosphonites, arsines, stibines, ethers, amines, amides, imines, sulfoxides, carboxyls, nitrosyls, pyridines, and thioethers.

In a preferred embodiment, each of $X^1$ and $X^2$, which may be the same or different, is a $C_3$–$C_{20}$ hydrocarbon chain with an allyl moiety as an end group bonded to the ruthenium atom. The hydrocarbon chain may be substituted on its backbone with up to three substituents independently selected from $C_1$–$C_{20}$ alkyl, $C_1$–$C_{20}$ alkoxy, and $C_6$–$C_{12}$ aryl groups. The allyl moiety may further have up to three functional groups independently selected from: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In another preferred embodiment, $X^1$ and $X^2$ together constitute the group resulting from the dimerization of an alkene, for example isoprene, said group resulting from the dimerization of an alkene optionally having on its backbone up to three substituents as described above, and further optionally having up to three functional groups as described above.

In a preferred embodiment, $L^1$ and $L^2$, which may be the same or different, are selected from phosphines, sulfonated phosphines, phosphites, phosphinites, phosphonites, arsines, stibines, ethers, amines, amides, imines, sulfoxides, carboxyls, nitrosyls, pyridines, and thioethers. In a more preferred embodiment, $L^1$ and $L^2$, which may be the same or different, are phosphines of the formula $PR^1R^2R^3$, wherein $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl. In a most preferred embodiment, $L^1$ and $L^2$, which may be the same or different, are $P(cyclohexyl)_3$, $P(cyclopentyl)_3$, $P(isopropyl)_3$, or $P(t-butyl)_3$.

In another embodiment, $L^1$ and $L^2$, which may be the same or different, are amines represented by the formula $NR^1R^2R^3$, wherein $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl. In such a preferred embodiment, $L^1$ and $L^3$, which may be the same or different, are $N(ethyl)_3$ or $N(methyl)_3$.

$L^1$ and $L^2$ taken together may also be a bidentate ligand coordinated to the central ruthenium atom through phosphorus, nitrogen, arsenic atoms or a combination thereof. The bidentate ligand preferably has up to 30 carbon atoms and up to 10 heteroatoms selected from phosphorus, nitrogen and arsenic. Examples of the bidentate ligand are 1,2-bis(diphenyl-phosphino)ethane, 1,2-bis(diphenylarsino) ethane, bis(diphenylphosphino)methane, ethylenediamine, propylenediamine, propylenediamine, diethylenediamine, arphos (i.e., arsine phosphine), phen (i.e., phenanthroline), bpy (i.e., bipyridine), and α di-imine. In such embodiment having a bidentate ligand, the $L^3$ ligand preferably is a solvent molecule, as described above, which may have an oxygen, nitrogen, sulfur, or selenium atom coordinating to the central ruthenium atom.

The $L^1$, $L^2$ and $L^3$ groups taken together may also be a tridentate ligand derived from phosphorus or nitrogen. An example of a suitable tridentate ligand is triphos.

In embodiments of the catalysts of the invention wherein $L^3$ is a solvent molecule, the solvent preferably is selected from THF, acetonitrile, pyridine, triethyl amine, and a thiol.

The anion A that is very weakly coordinated to the metal center may be derived from any tetra coordinated boron, such as $BF_4^-$, or hexa coordinated phosphorus, such as $PF_6^-$. The weakly coordinated anion A may also be any one of the following: $ClO_4^-$; fluorinated derivatives of $BPh_4^-$ such as $B(C_6F_5)_4^-$, $Ph_3BCNBPh_3^-$, carba-closo-dodecaborate $(CB_{11}H_{12}^-)$ and other carboranes, pentafluorooxotellurate $(OTeF_5^-)$; $HC(SO_2CF_3)_2^-$; $C_{60}^-$; $B(o-C_6H_4O_2)_2^-$; $H(1,8-BMe_2)_2C_{10}H_6^-$; or any of the anionic methylaluminoxanes.

Examples of preferred catalysts according to the invention are:

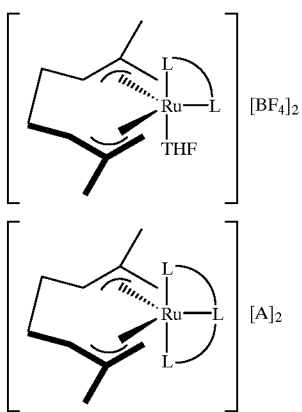

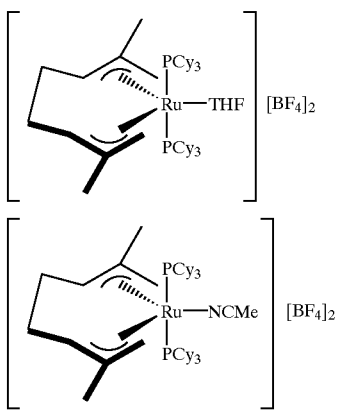

The catalysts of the invention may be prepared starting from allyl dimer complexes represented by the formula $[(X^1)(X^2)RuY_2]$ shown below, wherein $X^1$ and $X^2$ are allyl-containing groups as described above, and Y is a halide, for example chloride. A suitable allyl ruthenium dimer complex is $[(allyl)RuCl_2]$ wherein the allyl group is the 2,7 dimethyl-octadiene-diyl ligand, which may be prepared from isoprene and commercially available ruthenium (III) chloride, for example by the method disclosed in Schlund et al., *J. Am. Chem. Soc.*, 1989, 111, p. 8004.

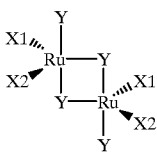

The two reactions schemes shown below may be followed for the synthesis of the complexes of the invention. Of those two methods, the simple one-pot method (Reaction Scheme B) may be used for preparing all the ruthenium catalysts of the invention from an $[(X1)(X2)RuY_2]_2$ dimer. Both processes result in good product yield without the need for expensive and sophisticated equipment. Furthermore, the methods can produce catalysts in a form which does not require post purification of the synthesized materials.

The one-pot synthesis is particularly convenient because the catalysts of the invention can be prepared by simply adding the appropriate reagents sequentially in stoichiometric quantities. Both procedures do not require the stringent methodologies typical of organometallic syntheses, and the formation of most of the complexes of the invention can be accomplished within a few hours in both procedures. Post purification of the isolated complexes is usually not required, and since the yield of these catalysts is typically greater than 90%, both synthesis methods are commercially viable.

The catalysts of the invention are synthesized by using a solvent that can favorably coordinate and occupy one of the coordination sites on the ruthenium atom. The solvent is required for maintaining the coordination geometry prior to the metathesis reaction, for example polymerization, but should dissociate quickly in the presence of the olefin, for example an olefin monomer being polymerized. In this regard, solvents with oxygen and nitrogen donors are preferred since they can dissociate easily in the presence of the olefin, and provide a vacant site for the olefin to coordinate to the central ruthenium atom.

General Synthetic Schemes

The ruthenium catalysts may be synthesized according to the reactions schemes described above, using readily available stable starting materials. In general, the formation of complexes of the invention can be completed in a few hours, and the percent yield obtained in most cases is good to excellent, typically greater than 80%. The reactions are sufficiently clean with practically no side or competing reactions occurring simultaneously. These preparations generally may be carried out at room temperature with minimum constraints. The general synthetic schemes are illustrated below for embodiments of the complexes represented by formula I, II and III.

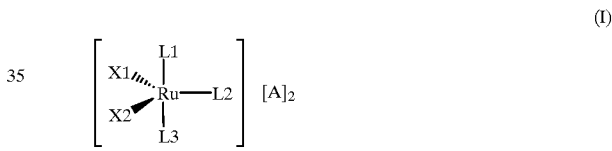

(I)

In a preferred embodiment of the catalyst represented by formula (I) above, $L^1$ and $L^2$ are tricyclohexyl phosphine, which are highly sterically encumbered neutral donor electron ligands; $L^3$ is THF which is a solvent capable of coordinating with the ruthenium central atom and is also a neutral donor ligand; $X^1$ and $X^2$ are the bidentate 2,7 dimethyl-octadiene-diyl ligand; and A is the $BF_4^-$ anion. The formation of this catalyst can be accomplished by contacting a ruthenium dimer complex as shown above (wherein M=Ru; $X^1$ and $X^2$ are the bidentate 2,7-dimethyl-octadiene-diyl ligand, and Y is the Cl ligand) with THF, a solvent that is capable of coordinating to the central ruthenium atom. To the resultant product a compound of the formula $B^+A^-$ is added to precipitate out the chloride salt. For example, $AgBF_4$ is used as the salt to precipitate out AgCl from the reaction. Finally, the neutral electron donor ligands $L^1$ and $L^2$ (for example, tricycloalkylphosphines) are added to the reaction system, and the complex catalyst is recovered as a product of the reaction.

In another aspect of the present invention, a solvent wherein the donor atom is nitrogen, such as acetonitrile or pyridine, is brought in contact with the ruthenium dimer complex. To the resulting solution, a compound of the formula $B^{+A-}$ is added to precipitate out the chloride salt. For example, $NH_4PF_6$ or $TlPF_6$ can be used as the salt for precipitating out $NH_4Cl$ or TlCl. Finally, a neutral electron donor ligand which possesses sterically encumbering substituents, such as tricyclohexylphosphine, is added to the solution, and the obtained complex catalysts are recovered.

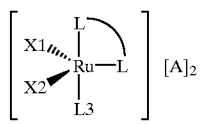
(II)

For preparing the catalyst of the present invention represented by formula (II), any neutral electron donor ligand that can coordinate to the central ruthenium atom in a bidentate fashion, for example bidentate ligands derived from phosphorus, nitrogen, arsenic or a combination of these (such as arphos) is used in the last step of the synthetic scheme.

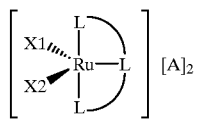
(III)

For preparing the catalyst on the present invention represented by formula (III), tridentate neutral donor ligands, such as tridentate ligands derived from phosphorus as well as nitrogen, are used in the last step of the synthetic scheme.

We have discovered two routes for synthesizing the complexes according to the invention, both of which result in practically quantitative yields. In both instances, the starting material is a ruthenium dimer complex represented by the formula $[(X1)(X2)RuY_2]$, such as an $[(allyl)RuCl_2]_2$ dimer complex wherein (allyl) is the 2,7 dimethyl-octadienediyl ligand. Those two synthetic schemes are further illustrated below with specific reagents.

halide salt is completed, the solution is filtered through a short column of Celite™ (2×2 cm), and to the eluate the neutral electron donor ligand is added. The reaction is allowed to continue for two hours at ambient temperature, preferably under a blanket of nitrogen or any inert gas. At the end of this period, the contents are evacuated under reduced pressure, and the crude solid obtained in this manner is washed with copious amounts of cold pentane. The complexes obtained this way are pure for most practical purposes and usually do not require additional purification procedures.

REACTION SCHEME B

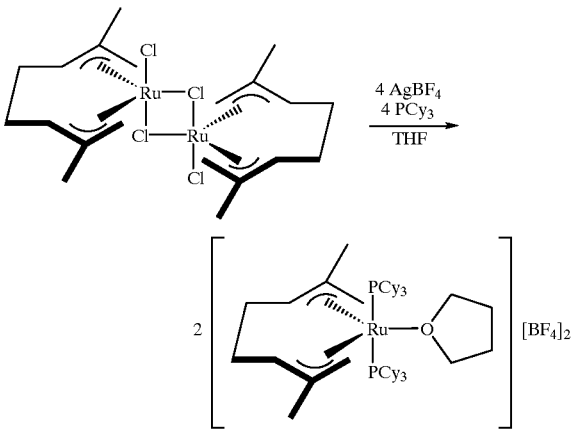

In the second route, Reaction Scheme B which is a one-step synthesis, the $[(allyl)RuCl_2]_2$ dimer complex is dissolved in an appropriate solvent, and a stoichiometric amount of $AgBF_4$, $NH_4PF_6$ or $TlPF_6$ (four equivalents) along with a stoichiometric quantity of the neutral electron

REACTION SCHEME A

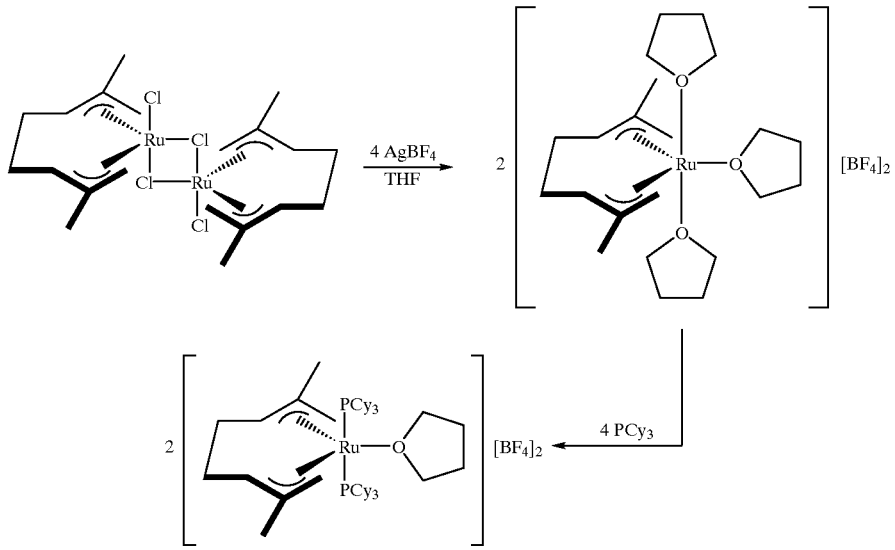

In the first route, Reaction Scheme A, the $[(allyl)RuCl_2]_2$ dimer complex is dissolved in THF and a stoichiometric amount of $AgBF_4$, $NH_4PF_6$ or $TlPF_6$ (four equivalents) is added to the stirring solution. After the precipitation of donor ligand (also four equivalents) are added all at the same time. The reaction is allowed to proceed at ambient temperature, preferably under a blanket of nitrogen or any inert gas for three hours, and at the end of this period the entire contents are filtered through a short column of Celite™ (2×2 cm). The filtrate is evacuated under reduced pressure and the crude product collected is washed (3×10 mL) with cold pentane. The catalyst obtained this way is also pure for all practical purposes.

The catalysts of the invention are stable in the presence of a variety of functional groups including hydroxyl, thiol, ketone, aldehyde, ester, ether, amine, imine, amide, nitro, carboxylic acid, disulfide, carbonate, isocyanate, carbodiimide, carboalkoxy, and halogen. Hence, the starting materials and products of the reactions described below may contain any one or more of these functional groups without poisoning the catalyst. Furthermore, these catalysts are stable in aqueous, organic, or protic solvents, for example aromatic hydrocarbons, chlorinated hydrocarbons, ethers, aliphatic hydrocarbons, alcohols, water, or mixtures of the above. Therefore, the preparations of the catalysts may be carried out in one or more of these solvents without poisoning the catalyst product.

The complex catalysts of the invention are effective in initiating metathesis reactions in olefins. In particular, they are highly effective catalysts for the polymerization of olefins, which may be cyclic or acyclic olefins, the latter having at least two double bonds in a molecule. The cyclic olefins may be monocyclic, bicyclic or tricyclic, and include ring-strained cyclic olefins such as norbornene and derivatives thereor, dicyclopendadiene and derivatives thereof, and trans-cyclooctadiene and derivatives thereof, as well as unstrained cyclic olefins including those having at least five carbon atoms in the ring such as cyclopentene, cycloheptene, trans-cyclooctene, etc. These olefins, whether cyclic or acyclic, may optionally have up to three substituents. Examples of such substituents are an alkyl group or a functional moiety such as hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate.

In a preferred embodiment of the invention, the complexes of the invention can initiate the ring opening metathesis polymerization (ROMP) of a cyclo-olefin monomer like NB without the use of any co-catalyst (such as a diazo alkyl compound). The ROMP of NB is practically instantaneous, and monomer to catalyst ratios of 10,000:1 effortlessly produce quantitative conversions. Even at ratios of up to 50,000:1 which were tried, the conversion had been extremely promising. For DCPD, however, we have discovered that it is critical for the catalyst to have at least one N donor ligand to exhibit robustness in the presence of the diazo alkyl compound. Therefore, a co-catalyst such as a diazo alkyl compound is required for the polymerization of DCPD.

Most of the complexes of the invention can be used in the presence of air. However, when oxygen and moisture are excluded from the system the activity demonstrated by these catalysts increases.

In a preferred embodiment of the invention, in-depth examination in our laboratory has revealed that when highly sterically encumbering ligands like tricyclohexylphosphine or triisopropylphosphine were coordinated to the ruthenium central atom, the catalyst could perform independently as an effective source for initiating the ROMP of NB without the use of a diazo alkyl compound. The rate of polymerization was found to be directly proportional to the magnitude of the steric bulk on the ligand, with tricyclohexylphosphine groups exhibiting the fastest rates. Furthermore, cycloalkyls or secondary alkyl substituents demonstrated a higher reactivity than aryl substituents for the same donor molecule.

The polymerizations were very rapid when phosphorus was the donor molecule, followed by nitrogen and arsenic with the same substituents. In the investigations of bidentate and tridentate donor ligands it was also discovered that the phosphines were the most reactive catalysts, followed by amines and arsines.

The following examples further illustrate aspects of the invention but do limit the invention. Unless otherwise indicate, all parts, percentages, rations, etc., in the examples and the rest of the specification are on the basis of weight.

Synthesis of $[(2,7\text{-dimethyloctadiene-diyl})Ru(PCy_3)(THF)_2][BF_4]_2$

METHOD A:

In general, unless explicitly noted otherwise, all solvents used are degassed prior to use.

The $[(2,7\text{-dimethyloctadienediyl})RuCl_2]_2$ dimer complex (1.0 gm, 1.62 mmols) was charged into a 50 mL Schlenk flask equipped with a magnetic stirrer inside an inert atmosphere glove-box. To the complex was then added ~30 mL dry THF and the solution was allowed to stir for about 20 minutes. 1.26 gm $AgBF_4$ (4 equivalents, 6.48 mmols) was carefully weighed out and added to the stirring solution. The color instantaneously changed first to dark grey and then to an olive color. The reaction was allowed to continue for ca. 2 hours. By the end of this period complete precipitation of AgCl had occurred. The flask was removed from the glove-box and the AgCl was filtered off using a short column of Celite™ (2×2 cm). To the filtrate was added 1.82 gm of $PCy_3$ (6.48 mmols) and the reaction was continued for an additional 4 hours at ambient temperature. At the end of this period, the solvent was evacuated under reduced pressure, and the crude solid that was collected was washed several times with generous amounts of cold pentane. The solid which had a pale green appearance was dried on the vacuum line overnight. The total yield was 2.81 gm (82%).

METHOD B: One-pot synthesis

The $[(2,7\text{-dimethyloctadienediyl})RuCl_2]_2$ dimer complex (1.0 gm, 1.62 mmols) was charged into a 50 mL Schlenk flask equipped with a magnetic stirrer inside an inert atmosphere glove-box. To the complex was added ~30 mL dry THF and the reaction was allowed to proceed for about 20 minutes. Next, 1.26 gm $AgBF_4$ (4 equivalents, 6.48 mmols) and 1.82 gm of $PCy_3$ (6.48 mmols) were added sequentially to the stirring solution. The reaction was allowed to continue for approximately 5 hours at ambient temperature, and at the end of this period the reaction solution was filtered through a short Celite™ column (2×2 cm). The filtrate was evacuated under reduced pressure, and the solid left behind was washed several times with copious amounts of cold pentane and dried overnight on a vacuum line to yield a pale green complex. The yield in this case was approximately the same (2.76 gm >80%) as that obtained from Method A. Characterization of the complex was carried out by $^1H$ and $^{31}P$ NMR.

Selective spectroscopic data for $[(2,7\text{-dimethyloctadienediyl})Ru(PCy_3)_2(THF)][BF_4]_2$:

$^1H$ NMR (300 MHz, $CDCl_3$)

| | |
|---|---|
| δ ppm = | 1.41(4H's), 1.55(8H's), 1.84(8H's), 2.02(10H's)$CH_2(PCy_3)$; 3.38(8H's)(THF); 3.70(s), 4.90(s), 5.05(d), 5.25(s), 6.62(d), 6.98(s) from octadienediyl ligand. |

$^{31}P$ NMR (121.4 MHz $CDCl_3$) d(ppm)=36.57 (s, $PCy_3$).

Synthesis of $[(2,7\text{-dimethyloctadienediyl-diyl})Ru(PCy_3)_2(NCMe)][BF_4]_2$ The formation of this complex was carried out in an analogous manner as that described above, except in this case the [(allyl)RuCl$_2$]$_2$ dimer complex was dissolved in ~30 mL acetonitrile. The formation of the complex can be carried out by both the methods described above. In a typical procedure, the dimer [((2,7-dimethyloctadienediyl-diyl)RuCl$_2$]$_2$ was dissolved in MeCN followed by addition of four molar equivalents of AgBF$_4$. After the complete precipitation of AgCl (approximately three hours), four equivalents of PCy$_3$ was added and the solution allowed to stir for an additional two hours. Filtration through a short column of Celite™ followed by evacuation of the filtrate under reduced pressure yielded the crude product which was recrystallized from CH$_2$Cl$_2$ and pentane by placing the flask in a dry-ice/acetone (–78° C.) bath for approximately 2 hours, which resulted in fine yellow crystals separating out.

Characterization of the complex was carried out by running its $^1$H NMR spectrum. Selective spectroscopic data for [(2,7-dimethyloctadienediyl)Ru(PCy$_3$)$_2$(NCMe)][BF$_4$]$_2$ in CDCl$_3$:

δ ppm={5.42; 5.12; 4.87(internal); 4.72(internal); 4.27; 4.00} all protons from the octadienediyl ligand; 2.93 (CH$_3$CN); 1.24–1.93 protons from tri-cyclohexyl phosphine.

Synthesis of [(2,7-dimethyloctadienediyl-diyl)Ru(solv)$_3$][BF$_4$]$_2$ wherein (solv)=THF; py; MeCN, NEt$_3$ A 50 mL Schlenk flask equipped with a magnetic stirrer, was charged with 150 mg (0.24 mmoles) of the (2,7-dimethyloctadienediyl)RuCl$_2$ dimer. 30 mL of the appropriate solvent (that had been previously dried by known methods) was added to this via syringe under a flow of argon. The flask was connected to an oil bubbler and the solution was stirred for approximately 20 minutes. Next, 189 mg (0.96 mmoles) AgBF$_4$ was weighed out and carefully added to the stirring solution. The reaction was allowed to continue for an additional 3 hours, after which the stirring was stopped to allow the precipitate of AgCl to settle to the bottom. During this period the color of the solution which was initially purple had changed to greenish-yellow. This solution was then filtered through a short column (1.5 cm×2.5 cm) of Celite™. The solvent was evacuated under reduced pressure, and the residue that was left behind was dissolved in CH$_2$Cl$_2$ (10 mL). The flask containing the CH$_2$Cl$_2$ solution was taken inside the glove-box and 15 mL cold pentane was added. Some solid was seen crashing out of solution immediately upon this addition. [Note: Instead of pentane, cold diethyl-ether (Et$_2$O) worked equally well.] The flask was left inside the freezer (–30° C.) in the glove-box overnight. The solid that precipitated out was collected the next day and dried on a high vacuum line. The total yield varied between ~60% and 70%. The mother liquor was evaporated to yield a brittle foam which was also collected inside the glove-box. This amounted to an additional 10%.

The THF substituted complex was not isolated as a solid like the others. In this case, after filtering off the AgCl precipitate, the complex was left inside the freezer (–30° C.) in the glove-box as a THF solution.

Synthesis of [(allyl)Ru(L$_2$)(THF)][BF$_4$]$_2$; [(allyl)Ru(L^L)(THF)][BF$_4$]$_2$; and (allyl)Ru(L^L^L)][BF$_4$]$_2$. wherein L=P$^i$Pr$_3$; L^L=Bpy; phen; N,N' Di-tert-butylethylenediamine and L^L^L=triphos and (allyl) is 2,7-dimethyloctadienediyl For the formation of these complexes the same procedure as that described above for the solvent substituted complex was followed except in this case the [(allyl)RuCl$_2$]$_2$ dimer was initially dissolved in dry THF, followed by addition of four equivalents of AgBF$_4$. To the stirring solution was added, after 3 hours four equivalents of the monodentate ligand (P$^i$Pr$_3$) or two equivalents of the bi-dentate ligand (Bpy; phen; N,N' di-tert-butylethylenediamine) or the tri-dentate ligand (triphos). After precipitation of AgCl was complete, the solution was filtered through a short column of Celite™ and evacuated under reduced pressure. The crude residue was dissolved in CH$_2$Cl$_2$ (10 mL), and Et$_2$O (15 mL) was added. The flask was left inside the freezer (–30° C.) in the glove-box overnight and the solid precipitate that crashed out of solution was collected on a frit (Schlenk technique) and dried on the high-vacuum line for several hours. The total product yield from this procedure was between 100–125 mg for most of the complexes.

Synthesis of [(allyl)Ru(NCMe)$_2$Cl][SbF$_6$]; [(allyl)Ru(NCMe)$_2$Cl][PF$_6$]

For the formation of these two complexes, the (allyl)RuCl$_2$ dimer was dissolved in acetonitrile and two equivalents of either AgSbF$_6$ or NH$_4$PF$_6$ was added respectively. After precipitation of AgCl or NH$_4$Cl had completed, the solution was filtered through a short column (2×2 cm) of Celite and the filtrate evaporated to dryness. The crude product was recrystallized using methylene chloride/pentane as described above. The total yield obtained for both complexes was approximately 100 mg (70% based on (allyl)RuCl$_2$ dimer).

Synthesis of [(allyl)Ru(PCy$_3$)$_2$(THF)][PF$_6$]$_2$ 150 mg (0.24 mmoles) [(allyl)RuCl$_2$]$_2$ dimer was charged into a 100 mL Schlenk flask equipped with a magnetic stirrer inside the glove-box, followed by addition of 40 mL dry THF via a 100 mL gas-tight syringe. The complex was allowed to stir for approximately 20 minutes and after this 157 mg (0.96 mmoles) NH$_4$PF$_6$ (or the appropriate quantity of TIPF$_6$) was added. Upon adding the hexafluorophosphate the color of the solution retained its original purple color. The mixture was allowed to stir for an additional 3 hours and then 274 mg (0.96 mmoles), i.e., four molar equivalents, of PCy$_3$ was added. No change in color was observed after the addition of the phosphine ligand. Hence, the reaction was allowed to continue for 60 hours. At the end of this time the solution was passed through a short column of Celite™. The filtrate was evacuated under reduced pressure, and the crude product that was recovered was dissolved in methylene chloride (15 mL). Addition of pentane (10 mL) resulted in some solid crashing out of solution. The flask was placed inside the freezer (–30° C.) in the glove-box overnight, and the solid that precipitated out was collected on a frit employing standard Schlenk technique. The total yield from this reaction was approximately 250 mg (88%) based on the ruthenium dimer.

Synthesis of [(allyl)Ru(NCMe)$_3$][PF$_6$]$_2$

A procedure similar to that described above for the formation of the [(allyl)Ru(NCMe)$_3$][BF$_4$]$_2$ complex was followed for the synthesis of this complex. Thus, 150 mg (0.24 mmoles) of the (allyl)RuCl$_2$ dimer was dissolved in 40 mL of dry acetonitrile, followed by addition of four molar equivalents (157 mg, 0.96 mmoles) of NH$_4$PF$_6$ (or the appropriate amount of TIPF$_6$). The reaction mixture was allowed to stir for approximately 3 hours and then filtered through a short column (2×2 cm) of Celite™. Evaporation of the solvent resulted in the crude product, which was dissolved in methylene chloride (15 mL) followed by addition of cold pentane (10 mL). Very fine yellow crystals were seen precipitating out, and this process was completed when the flask was left overnight inside the freezer (−30° C.) in the glove-box. The solid (200 mg ~70% based on the dimer) was collected and dried on a high vacuum line.

POLYMERIZATION OF CYCLO-OLEFIN MONOMERS USING RUTHENIUM COMPLEXES

EXAMPLE 1

Formation of Ring Opened Poly-norbornene Using the Ruthenium Catalysts

Polymerization of norbornene was carried out by adding the ruthenium catalysts, synthesized as described above, to the norbornene dissolved in $CH_2Cl_2$ (Table 1). 10 mg of the catalyst was weighed into a 10 mL volumetric flask and dissolved in $CH_2Cl_2$. 1 mL of this was added to the norbornene solution for each experiment. The solutions in all cases turned viscous almost immediately. The reactions were, however, allowed to continue for 1 at the end of that period MeOH was added to quench the reaction.

TABLE 1

Polymerization of NB using the [(allyl)Ru(PCy$_3$)$_2$(THF)][BF$_4$]$_2$ complex = [Ru]

| Expt # | Catalyst | Monomer | Ratio | Yield | Temp | Solvent |
|---|---|---|---|---|---|---|
| 1 | [Ru] | NB | 100:1 | Quantitative | Ambient | $CH_2Cl_2$ |
| 2 | ↓ | ↓ | 1000:1 | ↓ | ↓ | ↓ |
| 3 | ↓ | ↓ | 10,000:1 | ↓ | ↓ | ↓ |
| 4 | ↓ | ↓ | 50,000:1 | <50% | ↓ | ↓ |

Initial conditions of experiment: Catalyst=1 mg ($1.05 \times 10^{-3}$ mmols); Monomer (NB)=9.65 mg for 100:1; 96.3 mg for 1000:1; 963 mg for 10000:1; 4.82 gm for 50000:1. Solvent=5 mL. Time (for all polymerizations) was 60 minutes. Reaction was quenched with MeOH.

EXAMPLE 2

Formation of Ring-opened Poly-norbornene Using Ruthenium Catalysts in the Presence of Diazo-alkanes As described above, when the ROMP of norbornene was carried out with the ruthenium complexes in the presence of diazo-alkanes, the yields were very poor (Table 2).

TABLE 2

Polymerization of NB using the [(allyl)Ru(PCy$_3$)$_2$(THF)][BF$_4$]$_2$ complex = [Ru] in the presence of [N$_2$ = CHC(O)OEt]

| Expt # | Catalyst | Monomer | Ratio Ru:Diazo:Monomer | Yield | Temp | Solvent |
|---|---|---|---|---|---|---|
| 1 | [Ru] | NB | 1:0:10,000 | >80% | Ambient | $CH_2Cl_2$ |
| 2 | ↓ | ↓ | 1:200:10,000 | <10% | ↓ | ↓ |

Initial Conditions of Experiment: [Ru]=2 mg ($1.92 \times 10^{-3}$ mmoles); NB=1.76 gm (19.16 mmoles); diazo=molar equivalent (see Table). Solvent=5 mL.

EXAMPLE 3

Formation of Ring-opened Poly-norbornene Using the [(allyl)Ru(PCy$_3$)$_2$—(NCMe)][BF$_4$]$_2$ complex Using the above ruthenium complex the ROMP of norbornene was carried out (Table 3) Although good yields were obtained with this complex, they were slightly inferior to those obtained when the solvent molecule coordinated to the metal center was THF. It was discovered, however, that this complex exhibits robustness (as seen in later example below) in the presence of the diazo-alkane, unlike the THF coordinated ruthenium complex.

TABLE 3

Polymerization of NB using the [(allyl)Ru(PCy$_3$)$_2$(NCMe)][BF$_4$]$_2$ complex = [Ru]

| Expt # | Catalyst | Monomer | Ratio Ru:Monomer | Yield | Temp. | Solvent |
|---|---|---|---|---|---|---|
| 1 | [Ru] | NB | 1:10,000 | ~30% | Ambient | $CH_2Cl_2$ |
| 2 | ↓ | ↓ | 1:10,000 | ~80% | ↓ | ↓ |

Initial Conditions of Experiment: [Ruthenium]=2 mg ($1.98 \times 10^{-3}$ mmols); [NB]=1.82 gms (19.8 mmols); solvent=$CH_2Cl_2$; time for Expt #1=2 hours; and for Expt #2=5 hours; reaction quenched with MeOH.

EXAMPLE 4

Formation of Poly-dicyclopentadiene Using Ruthenium Complexes

The formation of poly-dicyclopentadiene was attempted using the ruthenium complex from Example 3. It was found that reasonably good yields of the polymer could be obtained in the presence of an excess amount of the diazo-alkane. Yet another interesting observation was the complex exhibited a slightly better performance when dissolved in MeOH (Table 4), as to being dissolved in $CH_2Cl_2$.

TABLE 4

Polymerization of DCPD using the [(allyl)Ru(PCy$_3$)$_2$(NCMe)][BF$_4$]$_2$ complex (hereinafter represented by [Ru]) in the presence of the diazo-alkane

| Expt # | Catalyst | Monomer | Ratio Ru:Diazo:Monomer | Yield | Temp. | Time in hours |
|---|---|---|---|---|---|---|
| 1 | [Ru] | DCPD | 1:0:2000 | 20% | Ambient | 48 |
| 2 | ↓ | ↓ | 1:0:2000 | 25% | ↓ | 24 |
| 3 | ↓ | ↓ | 1:200:2000 | 50% | ↓ | 2 |
| 4 | ↓ | ↓ | 1:200:2000 | 60% | ↓ | 2 |

Initial conditions of experiment: Catalyst=[Ru]=2 mg ($1.98 \times 10^{-3}$ mmols); [DCPD]=525 mg (3.97 mmols); solvent= $CH_2Cl_2$/MeOH (⅙v/v); [diazo]=[$N_2$=CHC(O)OEt] molar equivalent;

*Note: For Experiments #1 & 3 the catalyst was dissolved in $CH_2Cl_2$, whereas for Experiments #2 & 4 it was dissolved in MeOH

EXAMPLE 5

Formation of Poly-dicyclopentadiene Using Different Ruthenium Complexes in the Presence of the Diazo-alkane In this set of experiments a representative example of the ruthenium complex synthesized (as described in the text) was used to study the ROMP of DCPD in the presence of the diazo-alkane. Specific catalysts that were used (see FIG. 1 above) are as indicated: A=[(allyl)Ru(L^L)(THF)][BF4]$_2$ where (L^L)=N,N-dimethyl-tert-butylethylenediamine; B=[(allyl)Ru(Py)$_3$][BF$_4$]$_2$; C=[(allyl)Ru(NEt$_3$)][BF$_4$]$_2$ and D=[(allyl)Ru(PCy$_3$)$_2$(THF)][PF$_6$]$_2$.

It was found that most of the N substituted ligands exhibited robustness in the presence of the diazo-alkane. However, the THF substituted complex was not able to exhibit any potency in the presence of the diazo-alkane, and a paltry yield was obtained.

TABLE 5

Polymerization of dicyclopentadiene using different ruthenium complexes in the presence of [N₂ = CHC(O)OEt]

| Expt # | Ru Catalyst | Ratio Catalyst: Diazo:Monomer | Time | Temp | Yield |
|---|---|---|---|---|---|
| 1 | A | 1:200:2000 | 1 hour | Ambient | 15% |
| 2 | B | ↓ | ↓ | ↓ | 15% |
| 3 | C | ↓ | ↓ | ↓ | 20% |
| 4 | D | ↓ | ↓ | ↓ | 5% |

Initial Conditions of Experiment: [Ru]=2 mg in each case ("x" mmoles of the appropriate catalyst); [diazo] and [DCPD]=molar equivalent according to table; solvent= $CH_2Cl_2$/MeOH in a (1/5 v/v). Solubility=Most of the polymers obtained were partially soluble in toluene and THF, indicating some amount of gelation being present.

EXAMPLE 6

Formation of Poly-norbornene Using Different Ruthenium Complexes

As described in Example 5, the different ruthenium complexes were also used to study the ROMP of norbornene. In these polymerizations diazo-alkane was also not used. The experimental conditions for these polymerizations were kept the same as that for the $[(allyl)Ru(PCy_3)_2(THF)][BF_4]_2$ complex. It was found that under those conditions the percent yields (Table 6) were substantially lower. Specific catalysts used for these experiments were as follows:

A=$[(allyl)Ru(L^\smallfrown L)(THF)][BF_4]_2$, wherein $(L^\smallfrown L)$=N,N-dimethyltert-butylethylenediamine;

B=$[(allyl)Ru(py)_3][BF_4]_2$; C=$[(allyl)Ru(NEt_3)][BF_4]_2$;

D=$[(allyl)Ru(PCy_3)_2(THF)][PF_6]_2$; and

E=$[(allyl)Ru(triphos)][BF_4]_2$

TABLE 6

ROMP of norbornene using different ruthenium complexes

| Expt # | Ru Catalyst | Ratio Catalyst:Monomer | Time | Temp. | Yield |
|---|---|---|---|---|---|
| 1 | A | 1:10,000 | 1 hour | Ambient | 40% |
| 2 | B | ↓ | ↓ | ↓ | 40% |
| 3 | C | ↓ | ↓ | ↓ | 50% |
| 4 | D | ↓ | ↓ | ↓ | Quantitative |
| 5 | E | ↓ | ↓ | ↓ | ~30% |

Initial Conditions of Experiment: [Ru]=2 mg of ruthenium complex in each case ("x" mmoles of the appropriate catalyst); [NB]=molar equivalent according to table; solvent=$CH_2Cl_2$ ~5 mL; all reactions were quenched with MeOH after 1 hour.

What is claimed is:

1. A cationic complex represented by formula I, II or III:

$$[(X^1)(X^2)Ru(L^1)(L^2)(L^3)][A]_2 \quad (I)$$

$$[(X^1)(X^2)Ru(L^\smallfrown L)(L^3)][A]_2 \quad (II)$$

$$[(X^1)(X^2)Ru(L^\smallfrown L^\smallfrown L)][A]_2 \quad (III)$$

wherein each of $X^1$ and $X^2$, which may be the same or different, is a $C_3$–$C_{20}$ hydrocarbon group having an allyl moiety as an end group bonded to the ruthenium atom, optionally substituted with a $C_1$–$C_{20}$ alkyl, a $C_1$–$C_{20}$ alkoxy, or a $C_6$–$C_{12}$ aryl group on its backbone, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; or $X^1$ and $X^2$ together form a group which results from dimerization of an alkene and has at each end an allyl group bonded to the ruthenium atom, said group resulting from the alkene dimerization being optionally substituted on its backbone with a $C_1$–$C_{20}$ alkyl, a $C_1$–$C_{20}$ alkoxy, or a $C_6$–$C_{12}$ aryl group, and further optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen;

$L^1$ and $L^2$, which may be the same or different, are highly sterically encumbered monodentate neutral electron donor ligands;

$L^\smallfrown L$ is a bidentate neutral electron donor ligand;

$L^3$ is a solvent molecule coordinated to the central ruthenium atom or a monodentate neutral electron donor ligand;

$L^\smallfrown L^\smallfrown L$ is a tridentate neutral electron donor ligand; and

[A] is a counter anion weakly coordinated to the ruthenium atom.

2. A cationic complex according to claim 1, wherein each of $X^1$ and $X^2$, which may be the same or different, is a $C_3$–$C_{20}$ hydrocarbon group having an allyl moiety as an end group bonded to the ruthenium atom, optionally substituted with a $C_1$–$C_{20}$ alkyl, a $C_1$–$C_{20}$ alkoxy, or a $C_6$–$C_{12}$ aryl group on its backbone, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

3. A cationic complex according to claim 1, wherein $X^1$ and $X^2$ together form a group which results from dimerization of an alkene and has at each end an allyl group bonded to the ruthenium atom, said group resulting from the alkene dimerization being optionally substituted on its backbone with a $C_1$–$C_{20}$ alkyl, a $C_1$–$C_{20}$ alkoxy, or a $C_6$–$C_{12}$ aryl group, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

4. A cationic complex according to claim 1, wherein $L^1$ and $L^2$ are independently selected from the group consisting of phosphines, sulfonated phosphines, phosphites, phosphinites, phosphonites, arsines, stibines, ethers, amines, amides, imines, sulfoxides, carboxyls, nitrosyls, pyridines, and thioethers.

5. A cationic complex according to claim 1, wherein $L^1$ and $L^2$ are independently selected from the group consisting of phosphines of the formula $PR^1R^2R^3$, where $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl.

6. A cationic complex according to claim 5, wherein $L^1$ and $L^2$ are independently selected from the group consisting P(cyclohexyl)$_3$, P(cyclopentyl)$_3$, P(isopropyl)$_3$ and P(t-butyl)$_3$.

7. A cationic complex according to claim 1, wherein $L^1$ and $L^2$ are independently selected from the group consisting of amines of the formula $NR^1R^2R^3$, where $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl.

8. A cationic complex according to claim 7, wherein $L^1$ and $L^2$ are independently selected from the group consisting of $N(ethyl)_3$ and $N(methyl)_3$.

9. A cationic complex according to claim 1, wherein $L^3$ is a solvent molecule which has an oxygen, nitrogen, sulfur, or selenium atom coordinating to the central ruthenium atom.

10. A cationic complex according to claim 9, wherein $L^3$ is THF, acetonitrile, pyridine, tri-ethyl amine, or a thiol.

11. A cationic complex according to claim 1, wherein L⌢L is a bidentate neutral electron donor ligand containing at least one of phosphorus, nitrogen and arsenic.

12. A cationic complex according to claim 11, wherein $L^3$ is a solvent molecule which has an oxygen, nitrogen, sulfur, or selenium atom coordinating to the central ruthenium atom.

13. A cationic complex according to claim 1, wherein L⌢L⌢L is a tridentate ligand having as coordinating atom at least one of phosphorus and nitrogen.

14. A cationic complex according to claim 1, wherein the counterion [A] weakly coordinated to the central ruthenium atom has tetra coordinated boron or hexa coordinated phosphorus as a central atom.

15. A cationic complex according to claim 14, wherein the weakly coordinated counterion [A] is selected from the group consisting of $ClO_4^-$; fluorinated derivatives of $BPh_4^-$; $Ph_3BCNBPh_3^-$; carboranes; pentafluorooxotellurate ($OTeF_5^-$); $HC(SO_2CF_3)_2^-$; $C_{60}^-$; $B(o\text{-}C_6H_4O_2)_2^-$; $H(1,8\text{-}BMe_2)_2C_{10}H_6^-$ and methylaluminoxanes.

16. A cationic complex according to claim 1, wherein $L^3$ is a neutral electron donor ligand.

17. A cationic complex according to claim 16, wherein $L^1$ and $L^2$ are independently selected from the group consisting of phosphines, sulfonated phosphines, phosphites, phosphinites, phosphonites, arsines, stibines, ethers, amines, amides, imines, sulfoxides, carboxyls, nitrosyls, pyridines, and thioethers.

18. A cationic complex according to claim 17, wherein $L^1$ and $L^2$ are independently selected from the group consisting of phosphines of the formula $PR^1R^2R^3$, wherein $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl.

19. A cationic complex according to claim 17, wherein $L^1$ and $L^2$ are independently selected from the group consisting of amines of the formula $NR^1R^2R^3$, wherein $R^1$ is a $C_3$–$C_{12}$ secondary alkyl or a $C_5$–$C_{12}$ cycloalkyl group, and $R^2$ and $R^3$ are independently selected from the group consisting of a $C_6$–$C_{12}$ aryl, a $C_1$–$C_{10}$ primary alkyl, a $C_3$–$C_{12}$ secondary alkyl and a $C_5$–$C_{12}$ cycloalkyl.

20. A cationic complex according to claim 1, wherein $L^3$ is a solvent molecule coordinated to the central ruthenium atom.

21. A cationic complex according to claim 20, wherein $L^3$ is a solvent molecule which has an oxygen, nitrogen, sulfur, or selenium atom coordinating to the central ruthenium atom.

22. A cationic complex according to claim 21, wherein $L^3$ is THF, acetonitrile, pyridine, tri-ethyl amine, or a thiol.

23. A cationic complex according to claim 1, wherein $L^3$ is a monodentate neutral electron donor ligand.

24. A catalyst for metathesis reactions of olefins, said catalyst comprising a complex cation represented by formula I*, II* or III*:

$$[(X^1)(X^2)Ru(L^1)(L^2)(L^3)]^{+2} \qquad (I^*)$$

$$[(X^1)(X^2)Ru(L\frown L)(L^3)]^{+2} \qquad (II^*)$$

$$[(X^1)(X^2)Ru(L\frown L\frown L)]^{+2} \qquad (III^*)$$

wherein each of $X^1$ and $X^2$, which may be the same or different, is a $C_3$–$C_{20}$ hydrocarbon group having an allyl moiety as an end group bonded to the ruthenium atom, optionally substituted with a $C_1$–$C_{20}$ alkyl, a $C_1$–$C_{20}$ alkoxy, or a $C_6$–$C_{12}$ aryl group on its backbone, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; or $X^1$ and $X^2$ together form a group which results from dimerization of an alkene and has at each end an allyl group bonded to the ruthenium atom, said group resulting from the alkene dimerization being optionally substituted on its backbone with a $C_1$–$C_{20}$ alkyl, a $C_1$–$C_{20}$ alkoxy, or a $C_6$–$C_{12}$ aryl group, and further optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen;

$L^1$ and $L^2$, which may be the same or different, are highly sterically encumbered monodentate neutral electron donor ligands;

L⌢L is a bidentate neutral electron donor ligand;

$L^3$ is a solvent molecule coordinated to the central ruthenium atom or a monodentate neutral electron donor ligand; and L⌢L⌢L is a tridentate neutral electron donor ligand.

25. A catalyst according to claim 24, wherein each of $X^1$ and $X^2$, which may be the same or different, is a $C_3$–$C_{20}$ hydrocarbon group having an allyl moiety as an end group bonded to the ruthenium atom, optionally substituted with a $C_1$–$C_{20}$ alkyl, a $C_1$–$C_{20}$ alkoxy, or a $C_6$–$C_{12}$ aryl group on its backbone, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

26. A catalyst according to claim 24, wherein $X^1$ and $X^2$ together form a group which results from dimerization of an alkene and has at each end an allyl group bonded to the ruthenium atom, said group resulting from the alkene dimerization being optionally substituted on its backbone with a $C_1$–$C_{20}$ alkyl, a $C_1$–$C_{20}$ alkoxy, or a $C_6$–$C_{12}$ aryl group, said allyl moiety optionally having up to three functional groups independently selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

27. A catalyst according to claim 24, wherein $L^1$ and $L^2$ are independently selected from the group consisting of phosphines, sulfonated phosphines, phosphites, phosphinites, phosphonites, arsines, stibines, ethers, amines, amides, imines, sulfoxides, carboxyls, nitrosyls, pyridines, and thioethers.

28. A catalyst according to claim 24, wherein $L^1$ and $L^2$ are independently selected from the group consisting of phosphines of the formula $PR^1R^2R^3$, where $R^1$ is a $C_3-C_{12}$ secondary alkyl or a $C_5-C_{12}$ cycloalkyl group, and $R^2$ and $R^3$ are independently selected from the group consisting of a $C_6-C_{12}$ aryl, a $C_1-C_{10}$ primary alkyl, a $C_3-C_{12}$ secondary alkyl and a $C_5-C_{12}$ cycloalkyl.

29. A catalyst according to claim 28, wherein $L^1$ and $L^2$ are independently selected from the group consisting $P(cyclohexyl)_3$, $P(cyclopentyl)_3$, $P(isopropyl)_3$ and $P(t-butyl)_3$.

30. A catalyst according to claim 24, wherein $L^1$ and $L^2$ are independently selected from the group consisting of amines of the formula $NR^1R^2R^3$, where $R^1$ is a $C_3-C_{12}$ secondary alkyl or a $C_5-C_{12}$ cycloalkyl group, and $R^2$ and $R^3$ are independently selected from the group consisting of a $C_6-C_{12}$ aryl, a $C_1-C_{10}$ primary alkyl, a $C_3-C_{12}$ secondary alkyl and a $C_5-C_{12}$ cycloalkyl.

31. A catalyst according to claim 30, wherein $L^1$ and $L^2$ are independently selected from the group consisting of $N(ethyl)_3$ and $N(methyl)_3$.

32. A catalyst according to claim 24, wherein $L^3$ is a solvent molecule which has an oxygen, nitrogen, sulfur, or selenium atom coordinating to the central ruthenium atom.

33. A catalyst according to claim 32, wherein $L^3$ is THF, acetonitrile, pyridine, tri-ethyl amine, or a thiol.

34. A catalyst according to claim 24, wherein L^L is a bidentate neutral electron donor ligand containing at least one of phosphorus, nitrogen and arsenic.

35. A catalyst according to claim 34, wherein $L^3$ is a solvent molecule which has an oxygen, nitrogen, sulfur, or selenium atom coordinating to the central ruthenium atom.

36. A catalyst according to claim 24, wherein L^L^L is a tridentate ligand having as coordinating atom at least one of phosphorus and nitrogen.

37. A catalyst according to claim 24, wherein $L^3$ is a neutral electron donor ligand.

38. A catalyst according to claim 37, wherein $L^1$ and $L^2$ are independently selected from the group consisting of phosphines, sulfonated phosphines, phosphites, phosphinites, phosphonites, arsines, stibines, ethers, amines, amides, imines, sulfoxides, carboxyls, nitrosyls, pyridines, and thioethers.

39. A catalyst according to claim 38, wherein $L^1$ and $L^2$ are independently selected from the group consisting of phosphines of the formula $PR^1R^2R^3$, wherein $R^1$ is a $C_3-C_{12}$ secondary alkyl or a $C_5-C_{12}$ cycloalkyl group, and $R^2$ and $R^3$ are independently selected from the group consisting of a $C_6-C_{12}$ aryl, a $C_1-C_{10}$ primary alkyl, a $C_3-C_{12}$ secondary alkyl and a $C_5-C_{12}$ cycloalkyl.

40. A catalyst according to claim 38, wherein $L^1$ and $L^2$ are independently selected from the group consisting of amines of the formula $NR^1R^2R^3$, wherein $R^1$ is a $C_3-C_{12}$ secondary alkyl or a $C_5-C_{12}$ cycloalkyl group, and $R^2$ and $R^3$ are independently selected from the group consisting of a $C_6-C_{12}$ aryl, a $C_1-C_{10}$ primary alkyl, a $C_3-C_{12}$ secondary alkyl and a $C_5-C_{12}$ cycloalkyl.

41. A catalyst according to claim 24, wherein $L^3$ is a solvent molecule coordinated to the central ruthenium atom.

42. A catalyst according to claim 41, wherein $L^3$ is a solvent molecule which has an oxygen, nitrogen, sulfur, or selenium atom coordinating to the central ruthenium atom.

43. A catalyst according to claim 42, wherein $L^3$ is THF, acetonitrile, pyridine, tri-ethyl amine, or a thiol.

44. A catalyst according to claim 24, wherein $L^1$, $L^2$ and $L^3$ are neutral electron donor ligands.

45. A method for initiating a metathesis reaction of an olefin, comprising conducting the reaction in the presence of a cationic complex according to claim 1.

46. A method according to claim 45, wherein the olefin is a cyclic olefin and the metathesis reaction is ring-opening polymerization (ROMP).

47. A method according to claim 46, wherein the cyclic olefin is a norbornene monomer.

48. A method according to claim 46, wherein the cyclic olefin is a dicyclopentadiene monomer and the reaction is conducted in the presence of a diazo alkyl compound.

49. A method according to claim 48, wherein the diazo alkyl compound is $N_2=CHC(O)OEt$.

50. A method for initiating a metathesis reaction of an olefin, comprising conducting the reaction in the presence of a catalyst according to claim 24.

51. A method according to claim 50, wherein the olefin is a cyclic olefin and the metathesis reaction is ring-opening polymerization (ROMP).

52. A method according to claim 51, wherein the cyclic olefin is a norbornene monomer.

53. A method according to claim 51, wherein the cyclic olefin is a dicyclopentadiene monomer and the reaction is conducted in the presence of a diazo alkyl compound.

54. A method according to claim 53, wherein the diazo alkyl compound is $N_2=CHC(O)OEt$.

* * * * *